(12) United States Patent
Fischer, Jr.

(10) Patent No.: US 6,599,275 B1
(45) Date of Patent: *Jul. 29, 2003

(54) IMPLANTABLE MEDICAL DEVICE

(75) Inventor: Frank J. Fischer, Jr., Bloomington, IN (US)

(73) Assignee: Cook Incorporated, Bloomington, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/868,518

(22) Filed: Jun. 4, 1997

Related U.S. Application Data

(60) Provisional application No. 60/018,924, filed on Jun. 4, 1996.

(51) Int. Cl.[7] .............................................. A61M 5/32
(52) U.S. Cl. ...................................... 604/265; 424/422
(58) Field of Search ................................ 604/264, 265, 604/266, 280, 523, 891.1; 623/12; 424/422; 514/822; 523/112; 427/2

(56) References Cited

U.S. PATENT DOCUMENTS

| | | | | |
|---|---|---|---|---|
| 4,925,668 A | * | 5/1990 | Khan et al. ................ | 424/422 |
| 5,681,846 A | * | 10/1997 | Trissel ........................ | 514/449 |
| 5,820,607 A | * | 10/1998 | Tcholakian et al. ......... | 604/265 |
| 5,853,745 A | * | 12/1998 | Darouiche ................... | 424/423 |
| 5,902,283 A | * | 5/1999 | Darouche et al. ........... | 604/265 |

* cited by examiner

Primary Examiner—Brian L. Casler
Assistant Examiner—LoAn H. Thanh
(74) Attorney, Agent, or Firm—Brinks Hofer Gilson & Lione

(57) ABSTRACT

An implantable medical device 10 such as a catheter with a pharmacologically active ingredient layered between outer and inner elongated member tubes 11 and 13 for minimizing the risk of infection or other physiological afflictions associated with the implantation thereof. The outer and inner elongated member tubes include a base material mixed with a bioactive material including, for example, one and/or the other of rifampin and minocycline. An intermediate tube or layer 18 is positioned between and in communication with the outer and inner elongated member tubes 11 and 13. The intermediate tube or layer may also include a base material of, for example, silicone with a pharmacologically active ingredient mixed therein. The slower diffusion rate minocycline is included as or part of the bioactive material in the base material of the outer and inner elongated member tubes. The pharmacologically active ingredient or bioactive material such as a mixture of rifampin and minocycline is included in the base material of the intermediate tube or layer, which permeates through the inner and outer member tubes and diffuses therefrom or therethrough for treating tissues surrounding the catheter concomitantly.

2 Claims, 2 Drawing Sheets

IMPLANTABLE MEDICAL DEVICE

CROSS-REFERENCE TO RELATED COPENDING APPLICATIONS

This application claims priority of provisional application Ser. No. 60/018,924, filed Jun. 4, 1996.

TECHNICAL FIELD

This invention relates generally to medical devices and, particularly, to medical devices that are implantable either partly or completely into a human or veterinary patient.

BACKGROUND OF THE INVENTION

It has become common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a cannula, or the like. However, when such a device is introduced into and manipulated through the vascular system, the blood vessel walls can be disturbed or injured. Clot formation or thrombosis often results at the injured site, causing stenosis or occlusion of the blood vessel. Moreover, if the medical device is left within the patient for an extended period of time, a thrombus often forms on the device itself, again causing stenosis or occlusion. As a result, the patient is placed at risk of a variety of complications, including heart attack, pulmonary embolism, and stroke. Thus, the use of such a medical device can entail the risk of precisely the problems that its use was intended to ameliorate.

Another problem associated with implantable medical devices and, more particularly, to partly implanted medical devices such as catheters percutaneously introduced into the vascular system of a patient for long-term hemodialysis or drug infusion is the risk of infection. This risk is also present with hyperalimentation (intravenous feeding) catheters which are percutaneously introduced into the patient. The urinary tract is another system of the patient in which an urethral catheter such as a well-known Foley catheter is introduced into the patient's bladder via the urethra for the drainage of urine.

A recent attempt to reduce the risk of infection has been to coat the outer surface of the device with a bioactive material and/or pharmacologically active ingredient such as an antibiotic. Various coatings including antibiotics have been utilized, but have been found to disperse or dissipate from the coating in a relatively short period of time. Although effective in short-term implantation, such coatings are typically ineffective for extended duration placement such as with hemodialysis, drug infusion, or urinary tract catheters, which can be implanted in the patient for two to three years at a time.

The applicant has tested a partly implantable device containing an inner, elongated tube with an elongated outer sheath coaxially positioned around the inner tube, and with an intermediate space established between them. A mixture of drugs having different diffusion rates through the sheath and tube were positioned such as by injection, into the intermediate space. It was found that the higher diffusion rate drug quickly diffused through the inner tube and outer sheath without the benefit of the lower diffusion rate drug therewith for concomitantly combating the risk of infection.

SUMMARY OF THE INVENTION

The present invention is intended to provide a device in which at least two treatment materials reach the external or outer surfaces simultaneously. The implantable or partly implantable medical device includes a first elongated member or tube and a second elongated member or tube positioned adjacent to or within the first member or tube. A pharmacologically active ingredient is positioned between and in communication with the first and second elongated members. At least one of the first and second elongated members is permeable to the pharmacologically active ingredient for diffusing the pharmacologically active ingredient therethrough. A bioactive material preferably with a base material such as of at least one of the first and second elongated members is also provided, and the selected member(s) is permeable to the bioactive material for diffusing the bioactive material therefrom or therethrough.

When the pharmacologically active ingredient material includes a mixture of ingredients, the bioactive material can advantageously include one of the slower diffusion rate ingredients of the mixture, which is included in the base material of the selected member(s). This slower diffusion rate ingredient is then advantageously more readily accessible to the tissue surrounding the device for concomitant treatment with the other higher diffusion rate ingredient(s) of the mixture.

By way of example, the pharmacologically active ingredient advantageously and preferably includes a mixture of minocycline and rifampin, which is positioned between and in communication with the first and second elongated members of the implantable medical device. Minocycline has a lower diffusion rate than that of rifampin, and as a result, is included as the bioactive material in the base material in either one or both of the first and second elongated members. The higher diffusion rate rifampin permeates through the permeable base material of the elongated members and is diffused with the lower diffusion rate minocycline for concomitant treatment of tissue surrounding the outer surface of the catheter.

The thickness of the base material is advantageously selected to, in effect, slow down the diffusion of the higher diffusion rate ingredient so that the higher and lower diffusion rate ingredients are diffused from the medical device concomitantly for treatment of the tissues surrounding the device.

In one aspect of the invention, the implantable medical device includes a catheter having an outer elongated member with a passage extending longitudinally therein and an inner elongated member defining a passage extending longitudinally therein bounded by an inwardly directed surface of the inner elongated member, defining a lumen. The inner member is positioned in the passage of and surrounded by the outer elongated member, thus defining an intermediate region between the inner and outer elongated members. A pharmacologically active ingredient such, as minocycline, rifampin, or a mixture thereof is positioned in the intermediate region. As a result, the pharmacologically active ingredient is positioned between and in communication with the outer and inner elongated members. At least one of the outer and inner members, and preferably the outer member, is permeable to the pharmacologically active ingredient.

Applicant's improvement comprises including or mixing a bioactive material in the base material in at least one of the outer and inner members, which is permeable for diffusing therefrom or therethrough the bioactive material and/or the pharmacologically active ingredient from the intermediate space. The bioactive material can advantageously include the slower diffusion rate ingredient such as minocycline or pharmacologically active ingredient mixture.

In a preferred embodiment of the invention, the base material of the outer and inner members is silicone having a durometer in a range of 30 to 90 on the Shore A Hardness Scale. Preferably, the base material silicone has a durometer of 65 and is formed from a powder mixture with 7% minocycline by weight. A pharmacologically active ingredient such as a 50:50 mixture by weight of rifampin and minocycline is position in the intermediate region between the outer and inner coaxial members.

In another aspect of this invention, the intermediate region may comprise an elongated member or layer having a base material and that is positioned between the outer and inner elongated members, and the 50:50 mixture by weight of rifampin and minocycline is included or mixed with a base material of an intermediately positioned member or layer to a concentration of 7% by weight. The base material of the intermediately positioned member or layer can also include silicone, which is readily positioned or formed with the outer and inner coaxially positioned members. Advantageously, the outer member is in contact with the tissue of the patient of which fluid from the patient permeates through the catheter for diffusing the pharmacologically active ingredient and/or the bioactive material from the catheter.

In the preferred embodiment of the invention, an inner elongated member tube comprises a base material of silicone having 7% by weight minocycline included therein. An intermediate member or layer is positioned or formed over the inner member tube. The intermediate member or layer preferably includes a base material such as silicone and a 7% by weight mixture of 50:50 rifampin and minocycline. The outer elongated member tube also preferably comprises a base material of, for example, silicone and 7% by weight minocycline, which is positioned over the intermediate layer and inner member tubes. The overall wall thickness of the catheter is approximately one-quarter of that of the outside diameter of the catheter. As a result, the passage or lumen of the catheter is approximately one-half of its outside diameter. The wall thickness of the inner and outer elongated member tubes or layers is approximately the same, whereas the thickness of the intermediate layer is approximately two and one-half times that of either the inner or outer elongated member tubes or layers. The outside diameter of the preferred catheter falls within a range of 3 French to 18 French (0.039" to 0.236").

Detailed Description

Figure 1:
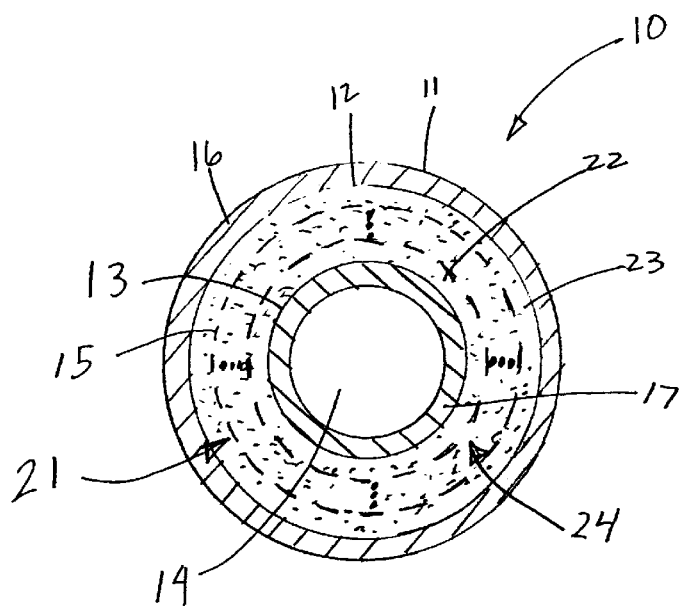
FIG. 1 depicts a cross-sectioned end view of a preferred illustrative embodiment of the implantable medical device of the present invention.

FIG. 1 depicts a cross-sectioned end view of a preferred illustrative embodiment of implantable medical device 10 such as a catheter having an outer, elongated member tube 11 with passage 12 extending longitudinally therein. Alternatively, outer elongated member tube can be simply a first layer 11 of material. Positioned preferably concentrically in passage 12 is inner elongated member tube 13 with passage 14 extending longitudinally therein. Again, alternatively, the inner elongated member tube can be simply a second layer 13 of material adjacent to or within first layer 11. An intermediate region 21 is defined between and in communication with the outer and inner elongated member tubes or layers 11 and 13 with intermediate region 21 comprising a pharmacologically active ingredient 15. The pharmacologically active ingredient is any drug, medicament, or agent or mixtures thereof, for treating infections or other physiological afflictions encountered with or due to the placement of such implantable medical devices. Preferably, this pharmacologically active ingredient includes one or more drugs, agents, or medicaments for concomitantly minimizing or treating the infection or affliction. Preferably, this pharmacologically active ingredient would include a 50:50 mixture by weight of minocycline- and rifampin. Minocycline has a lower diffusion rate than rifampin and, as a result, is also preferably mixed in the base silicone material 16 of outer member tube 11 as or part of the bioactive material. The minocycline of the pharmacologically active ingredient is also preferably included in the base silicone material 17 of inner elongated member tube 13. Minocycline 7% by weight in a powdered form is mixed with a powdered form of silicone and a solvent to form a liquid that is extruded into outer and inner member tubes 11 and 13. A desired length of the member tubes is cut to form the overall length of the catheter. One end of the catheter tubes is bonded together with a medical grade silicone adhesive. By way of example, outer elongated member tube is approximately 0.125" in diameter with a wall thickness of approximately 0.007". Inner elongated member tube 13 has an inner diameter of approximately 0.062" with a wall thickness of 0.007". The pharmacologically active ingredient comprising a 50:50 mixture by weight of rifampin and minocycline is positioned by being for example, poured, or injected into the intermediate space between the inner and outer elongated member tubes 13 and 11. As a result, the wall or layer thickness of the pharmacologically active ingredient mixture is approximately 0.017". The overall wall thickness of the catheter is approximately 0.031".

Base silicone material 16 and 17 of the outer and inner members is a silicone material having a durometer in a range of 30 to 90 on the Shore A Hardness Scale. Preferably, the minocycline and silicone mixture also has an overall durometer of 65 on the Shore A Hardness Scale. Base silicone material 16 and 17 is commercially available from the NU-SIL Corporation of Carpinteria, Calif.

Figure 2:
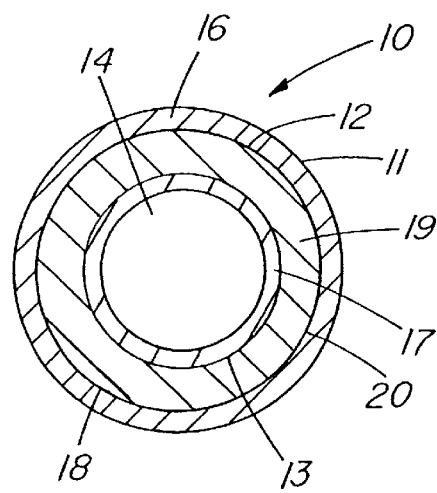
FIG. 2 depicts a cross-sectioned end view of another preferred embodiment of the implantable medical device of the present invention.

FIG. 2 depicts a second preferred embodiment of implanted medical device 10 such as a catheter with outer elongated member tube 11 and inner elongated member tube 13 positioned in passage 12 of outer elongated member tube 11. An intermediate layer or tube 18 of a base material such as silicone is positioned between outer and inner elongated member tubes 11 and 13 and in the intermediate region 21 space therebetween. Base material 16, 17 and 19 of outer, inner and intermediate layer tubes 11, 13 and 18 is a medical grade silicone material from the NU-SIL Corporation. The 7% minocycline is included in base material 16 and 17 of outer and inner member tubes 11 and 13. Base silicone material 19 includes a bioactive material such as a 50:50 mixture by weight of rifampin and minocycline. This bioactive material mixture is 7% by weight of the base silicone material 19. The wall thickness of the inner, outer and intermediate layer tubes is as previously described to permit the higher diffusion rate of rifampin to mix and permeate through the layers and out the outwardly directed and inwardly directed surfaces of the catheter concomitantly.

It is intended that the term bioactive material includes any material that is molecularly interactive with the fluids, cells, proteins or tissues of an animal including humans to augment the diagnosis, treatment or prevention of any physiologic or pathologic condition. It is further intended that this term includes therapeutic and diagnostic agents such as, for example, drugs, vaccines, hormones, steroids, proteins, previously described agents, complexing agents, salts, chemical compounds, polymers, and the like.

The base silicone material is a powdered material that is mixed with the bioactive material and/or the pharmacologically active ingredient in a well-known solvent. The mixture is then extruded at low temperatures with the solvent evaporating therefrom as the silicone material cures. This low temperature silicone is utilized so as not to evaporate the pharmacologically active ingredient and/or the bioactive material.

Figure 3:
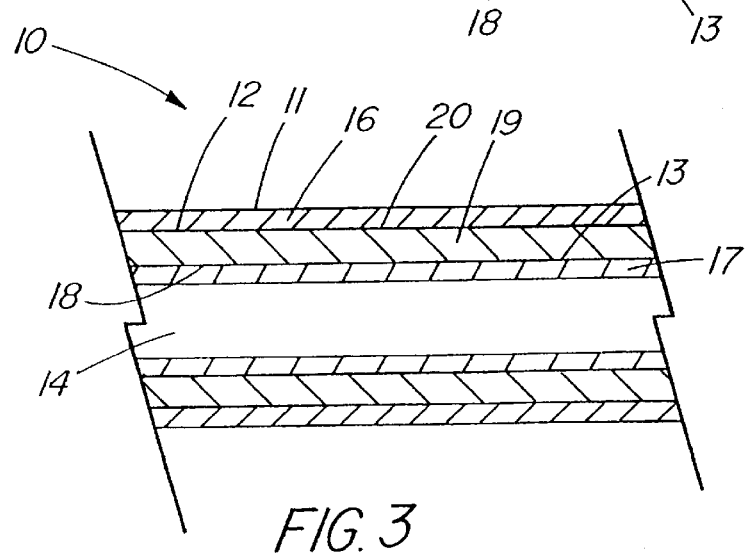
FIG. 3 depicts a partial, sectioned side view of the implantable medical device of FIG. 2.

FIG. 3 depicts a partial, sectioned side view of medical device 10 of FIG. 2. Outer and inner elongated member tubes are likewise shown with intermediate tube or layer 18 positioned in intermediate region 21 therebetween and in communication therewith. Passage 14 of the catheter is approximately one-half the outside diameter of catheter 10. As previously discussed, the overall wall thickness of catheter 10 is approximately 0.062". The outside diameter of the catheter is again 0.025". Intermediate tube or layer 18 is approximately two and one-half times the wall thickness of inner and outer elongated member tubes 13 and 11. Inner elongated member tube 13 is first extruded, with intermediate tube or layer 18 extruded, namely positioned, thereover. Outer elongated member tube 11 is then extruded over the intermediate and inner elongated member tubes. The intermediate layer is thus positioned between the inner and outer tubes.

With continued reference to FIGS. 1–3, implantable medical device 10 of the present invention comprises at least one bioactive material mixed with base material 16, 17 and/or 19 of outer, inner and/or intermediate layers 13, 11 and 18. In an alternative embodiment, at least one bioactive material can also be on outer surface 20 of intermediate layer 18. The other surfaces of the outer, inner, and intermediate layers or the layers themselves can either contain no bioactive material or contain one or more different bioactive materials. In this manner, one or more bioactive materials or drugs may be delivered, for example with a vascular stent or catheter, to the blood stream from the inwardly directed or lumen surface of the stent, and a different treatment can be delivered on the outwardly directed or vessel surface of the stent. A vast range of drugs, medicaments and materials can be employed as the bioactive material in one or more base material layers 16, 17 and 19, so long as the selected material can survive exposure to the placement or extrusion process or to a vacuum drawn during vapor deposition or plasma deposition. Particularly useful in the practice of the present invention are materials which prevent or ameliorate abrupt closure and restenosis of blood vessels previously opened by stenting surgery or other procedures. Thrombolytics (which dissolve, break up or disperse thrombi) and antithrombogenics (which interfere with or prevent the formation of thrombi) are especially useful bioactive materials when the implantable medical device 10 is a vascular stent. Particularly preferred thrombolytics are urokinase, streptokinase, and the tissue plasminogen activators. Particularly preferred antithrombogenics are heparin, hirudin, and the antiplatelets.

Urokinase is a plasminogen activating enzyme typically obtained from human kidney cell cultures. Urokinase catalyzes the conversion of plasminogen into the fibrinolytic plasmin, which breaks down fibrin thrombi.

Heparin is a mucopolysaccharide anticoagulant typically obtained from porcine intestinal mucosa or bovine lung. Heparin acts as a thrombin inhibitor by greatly enhancing the effects of the blood's endogenous antithrombin III. Thrombin, a potent enzyme in the coagulation cascade, is key in catalyzing the formation of fibrin. Therefore, by inhibiting thrombin, heparin inhibits the formation of fibrin thrombi. Alternatively, heparin can be covalently bound to the outer layer of implantable medical device 10. Thus, heparin would form the outermost layer of implantable medical device 10 and would not be readily degraded enzymatically, and would remain active as a thrombin inhibitor.

Of course, bioactive materials having other functions can also be successfully delivered by the device 10 of the present invention. For example, an antiproliferative agent such as methotrexate will inhibit over-proliferation of smooth muscle cells and thus inhibit restenosis of the dilated segment of the blood vessel. The antiproliferative is desirably supplied for this purpose over a period of about four to six months. Additionally, localized delivery of an antiproliferative agent is also useful for the treatment of a variety of malignant conditions characterized by highly vascular growth. In such cases, the device 10 of the present invention could be placed in the arterial supply of the tumor to provide a means of delivering a relatively high dose of the antiproliferative agent directly to the tumor.

A vasodilator such as a calcium channel blocker or a nitrate will suppress vasospasm, which is common following angioplasty procedures. Vasospasm occurs as a response to injury of a blood vessel, and the tendency toward vasospasm decreases as the vessel heals. Accordingly, the vasodilator is desirably supplied over a period of about two to three weeks. Of course, trauma from angioplasty is not the only vessel injury which can cause vasospasm, and the device 10 can be introduced into vessels other than the coronary arteries, such as the aorta, carotid arteries, renal arteries, iliac arteries or peripheral arteries for the prevention of vasospasm in them.

A variety of other bioactive materials are particularly suitable for use when the device 10 is configured as something other than a coronary stent. For example, an anti-cancer chemotherapeutic agent can be delivered by the device 10 to a localized tumor. More particularly, the device 10 can be placed in an artery supplying blood to the tumor or elsewhere to deliver a relatively high and prolonged dose of the agent directly to the tumor, while limiting systemic exposure and toxicity. The agent may be a curative, a pre-operative debulker reducing the size of the tumor, or a palliative which eases the symptoms of the disease. It should be noted that the bioactive material in the present invention is delivered across the device 10, and not by passage from an outside source through any lumen defined in the device 10, such as through a catheter employed for conventional chemotherapy. The bioactive material of the present invention can, of course, be released from the device 10 into any lumen defined in the device, or to tissue in contact with the device and that the lumen may carry some other agent to be delivered through it. For example, tamoxifen citrate, Taxol® or derivatives thereof, Proscar®, Hytrin®, or Eulexin® can be applied to the tissue-exposed surface of the device for delivery to a tumor located, for example, in breast tissue or the prostate.

Dopamine or a dopamine agonist such as bromocriptine mesylate or pergolide mesylate is useful for the treatment of neurological disorders such as Parkinson's disease. The device 10 could be placed in the vascular supply of the thalamic substantia nigra for this purpose, or elsewhere, localizing treatment in the thalamus.

A wide range of other bioactive materials can be delivered by the device 10. Accordingly, it is preferred that the bioactive material contained in or posited on the layer 18 includes at least one of heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; Hytrin® or other antihypertensive agents; an antimicrobial agent or antibiotic; aspirin, ticlopidine, a glycoprotein IIb/IIIa inhibitor or another inhibitor of surface glycoprotein receptors, or another anti-platelet agent; colchicine or another antimitotic, or another microtubule inhibitor, dimethyl sulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; tamoxifen citrate, Taxol® or the derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin or another immunosuppressive agent; trapidal (a PDGF antagonist), angiopeptin (a growth hormone antagonist), angiogenin, a growth factor or an anti-growth factor antibody, or another growth factor antagonist; dopamine, bromocriptine mesylate, pergolide mesylate or another dopamine agonist; $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-aminosteroid (lasaroid) or another free radical scavenger, iron chelator or antioxidant; a $^{14}$C-, $^3$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium, Norvir® Crixivan® or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs; Proscar®, Hytrin® or other agents for treating benign prostatic hyperplasia (BHP) or a mixture of any of these; and various forms of small intestine submucosa (SIS).

It is to be understood, however, that the above-described implantable medical device is merely an illustrative embodiment of the principles of this invention, and that other devices and methods for using them may be devised by those skilled in the art, without departing from the spirit and scope of the invention. It is to be understood that the invention is directed to embodiments both comprising and consisting of the disclosed parts. It is contemplated that only parts of the device can include the bioactive material and/or the pharmacologically active ingredient. Furthermore, different parts of the device can include different bioactive materials. It is also contemplated that different sides or regions of the same part of the device can include different bioactive materials or layers.

The intermediate layers 21 and 18 can comprise a single or, one treatment material with a higher diffusion rate, with or without a base material added thereto, whilst another treatment material with a slower diffusion rate is nearer to the outer surface of the device, to enable the treatment materials to achieve the objective of reaching the "outer surfaces" substantially simultaneously. The other treatment materials, can be located on the tubes or in the tubes or form parts of the tubes, and because of their particular positioning, they will reach the outer surfaces substantially simultaneously with the one treatment material.

Alternatively, the intermediate region 21 can comprise layers deposited between the inner and outer elongated member tubes (see FIG. 1), and such layers can each comprise a plurality of the treatment materials. The latter can be mixed together preferably with a base material, but the treatment materials can also be formed in layers with the higher diffusion rate treatment material being more concentrated at the center of the intermediate layer.

This concentration effect can be achieved in a variety of ways but it is preferred that the outermost layer 23 of the intermediate region be of the one material and the innermost layer 22 be of the other material, and the layer(s) 24 therebetween be of appropriate mixed percentage(s) with the percentages of the other material(s) increasing in proportion as the outermost layer is approached.

These layers may or may not contain base material the intermediate region may thus comprise at least a major percentage of the treatment materials or even consist entirely thereof, and may contain a mixture of faster and slower diffusion rate materials.

Any of the above devices may include outer tubes containing base material and only slower diffusion rate material (s), but it is to be understood that the tubes can contain higher and slower diffusion rate materials with the slower rate materials being more in evidence nearer the said outer surfaces.

Figure 4:
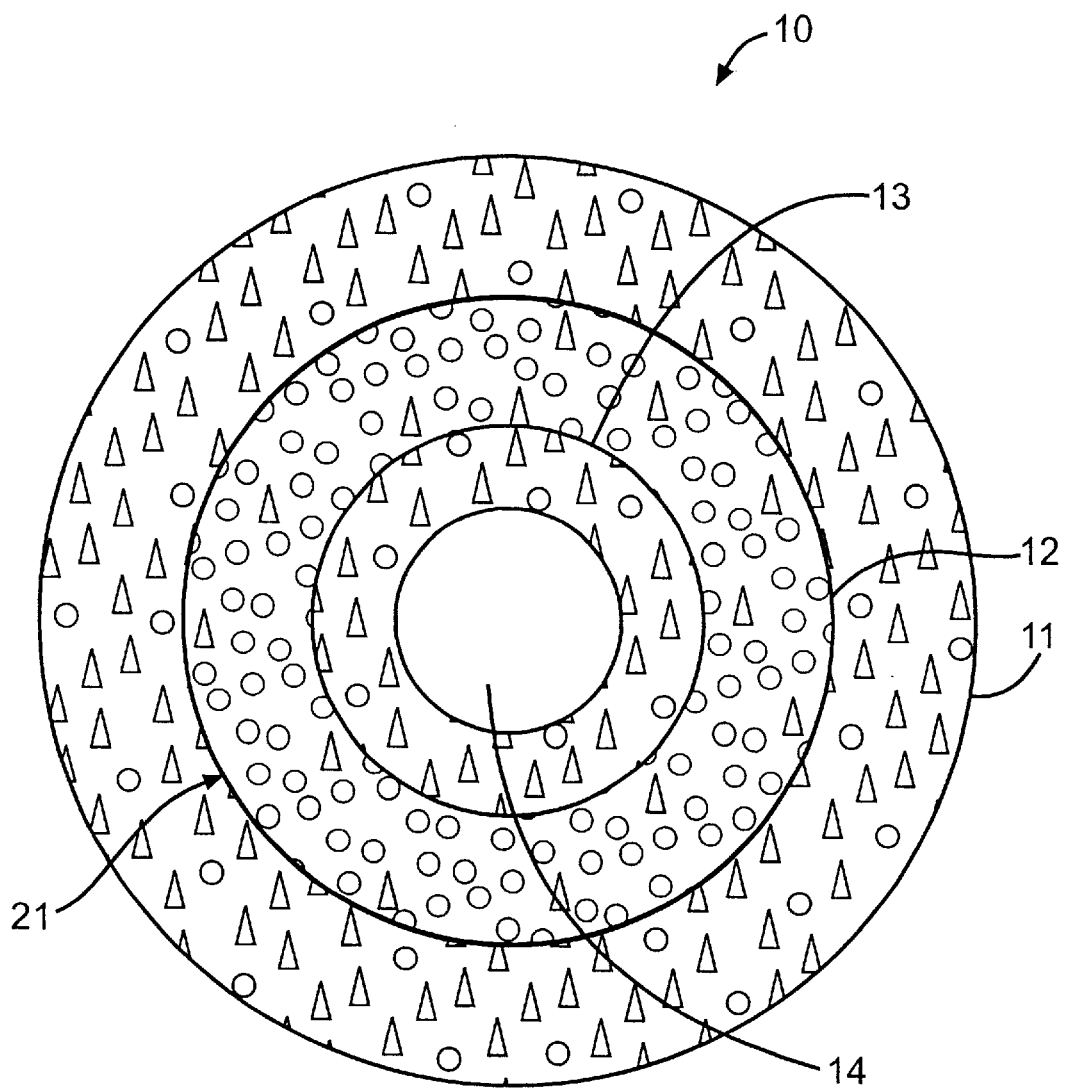
FIG. 4 depicts a cross-sectioned view of the implantable medical device of the present invention in which the inner and outer tubes contain a greater concentration of slower diffusion rate treatment materials than of faster diffusion rate materials, and the intermediate region contains a greater concentration of faster diffusion rate materials.

At least one of the inner and outer tubes may contain a greater concentration of the slower diffusion rate material than the faster diffusion rate material, as seen in FIG. 4 wherein both tube do so, with the slower rate material shown by the symbol Δ and the faster rate material is shown as ○ and is contained mostly in the intermediate region. The intermediate region and at least one of the inner and outer tubes may contain a major percentage of base material and a minor percentage of the treatment materials. Within a device, all or most of the slower diffusion rate material may be contained in the base material of the inner and outer tubes, while all or most of the faster diffusion rate material may be contained in the intermediate region.

Channels can be formed in the device through either the intermediate layer or through the inner and outer tubes, or both.

The channels can be permanently filled with treatment material or they can be used to supply a further treatment material each as liquid to a particular part of a patient when the device is positioned within the patient.

Alternatively, a balloon can be attached to the outer surface of the outer tube and inflated by further treatment material.

What is claimed is:

1. A medical device for at least partial implantation within a patient and having outwardly and inwardly directed surfaces, comprising first and second tubes of base material, one within the other, and a plurality of treatment materials contained within the device with one thereof having a respective diffusion rate and another thereof tending to have a respective rate of diffusion slower than that of the one material, said base material of at least one of said first and second tubes being permeable to said treatment materials permitting diffusion thereof to a respective at least one of said outwardly and inwardly directed surfaces at respective diffusion rates, at least part of one of said treatment materials being in a region between the first and second tubes, and wherein said one and said another of said treatment materials are at least distributed or positioned within the device, or within at least one of the first and second tubes, or within both said tubes, in such a way that said treatment materials tend to diffuse to said at least one of said outwardly and inwardly directed surfaces of the device approximately simultaneously;

wherein said at least one of the first and second tubes contain a mixture of said one and said another of said treatment materials;

wherein said region contains a mixture of said one and said another of said treatment materials, and the first and second tubes contains a greater concentration of said another of said treatment materials than of said one of said treatment materials; and wherein said region and said at least one of the first and second tubes contain a major percentage of said base material and a minor percentage of said treatment materials.

2. The device according to claim 1, wherein said inwardly directed surface of the device is formed from a mixture of said another of said treatment materials and silicone.

* * * * *